(12) United States Patent
Kim

(10) Patent No.: US 10,288,680 B2
(45) Date of Patent: May 14, 2019

(54) METHOD AND SYSTEM FOR MONITORING QUALITY AND CONTROLLING AN ALTERNATING CURRENT POWER SUPPLY PROVIDED TO AN ULTRASOUND SYSTEM FROM A POWER OUTLET

(71) Applicant: General Electric Company, Schenectady, NY (US)

(72) Inventor: Hyun Chul Kim, Seongnam (KR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 26 days.

(21) Appl. No.: 15/730,896

(22) Filed: Oct. 12, 2017

(65) Prior Publication Data

US 2019/0113567 A1    Apr. 18, 2019

(51) Int. Cl.
```
G01R 31/40       (2014.01)
G01R 31/317      (2006.01)
A61B 8/00        (2006.01)
G01R 31/3185     (2006.01)
```
(52) U.S. Cl.
CPC .......... *G01R 31/31721* (2013.01); *A61B 8/56* (2013.01); *G01R 31/318577* (2013.01)

(58) Field of Classification Search
CPC ..... G01R 31/34; G01R 31/343; G01R 31/346
See application file for complete search history.

(56) References Cited

U.S. PATENT DOCUMENTS

2016/0252549 A1*  9/2016  Worou .................. G01R 19/04
                                                       324/103 R
2018/0196098 A1*  7/2018  Ferguson ............. G01R 31/024

OTHER PUBLICATIONS

SimpleLink™ Wi-Fi® CC3200 Smart Plug Design Guide, "TI Designs", Texas Instruments, TIDU983—Jul. 2015, pp. 1-41.

* cited by examiner

*Primary Examiner* — Tung X Nguyen
(74) *Attorney, Agent, or Firm* — McAndrews, Held & Malloy, Ltd.; Jacob Groethe; David Bates

(57) ABSTRACT

A system and method for monitoring quality and controlling an AC power supply provided to medical equipment from a power outlet is provided. The method includes analyzing a digital signal to determine AC power supply quality characteristics of a corresponding AC power input received and converted to the digital signal at an AC power supply quality monitoring system. The method includes presenting the AC power supply quality characteristics at a display of the AC power supply quality monitoring system. The method includes determining whether the AC power supply quality characteristics are within a threshold quality range. The method includes activating a block at a protection circuit of the AC power supply quality monitoring system if the AC power supply quality characteristics are outside of the threshold quality range. The block at the protection circuit prevents the AC power input from being output from the AC power supply quality monitoring system.

20 Claims, 3 Drawing Sheets

METHOD AND SYSTEM FOR MONITORING QUALITY AND CONTROLLING AN ALTERNATING CURRENT POWER SUPPLY PROVIDED TO AN ULTRASOUND SYSTEM FROM A POWER OUTLET

FIELD

Certain embodiments of the disclosure relate to monitoring and controlling alternating current (AC) power supplies. More specifically, certain embodiments of the disclosure relate to a method and system for analyzing and presenting AC power supply quality characteristics employed to regulate the AC power supply.

BACKGROUND

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image.

Ultrasound systems are typically powered via a power distribution unit that distributes power received from an alternating current (AC) power supply, such as by inserting an ultrasound system plug into a socket of a power outlet. The quality of the power provided to the ultrasound system may have an impact on the operation of the system and the quality of images provided by the system. Power supply characteristics such as amplitude of the voltage, frequency, waveform, harmonic distortion, and electrical noise, among other things, may be representative of the quality of the power. For example, a decrease in the amplitude of the voltage (i.e., voltage sag) may cause artifacts to appear in images, equipment to lock up, and/or data to be scrambled or lost. An increase in the amplitude of the voltage (i.e., voltage surge) may introduce image artifacts, destroy electrical components, and/or cause the ultrasound system to malfunction. As another example, non-sinusoidal voltages can cause image artifacts, data to be lost and/or ultrasound systems to fail. Harmonic currents may cause overheating of neutral conductors and transformers, which may result in a failure of the ultrasound system. Electrical noise may introduce artifacts in acquired ultrasound image data.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for monitoring quality and controlling an AC power supply provided to medical equipment from a power outlet, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
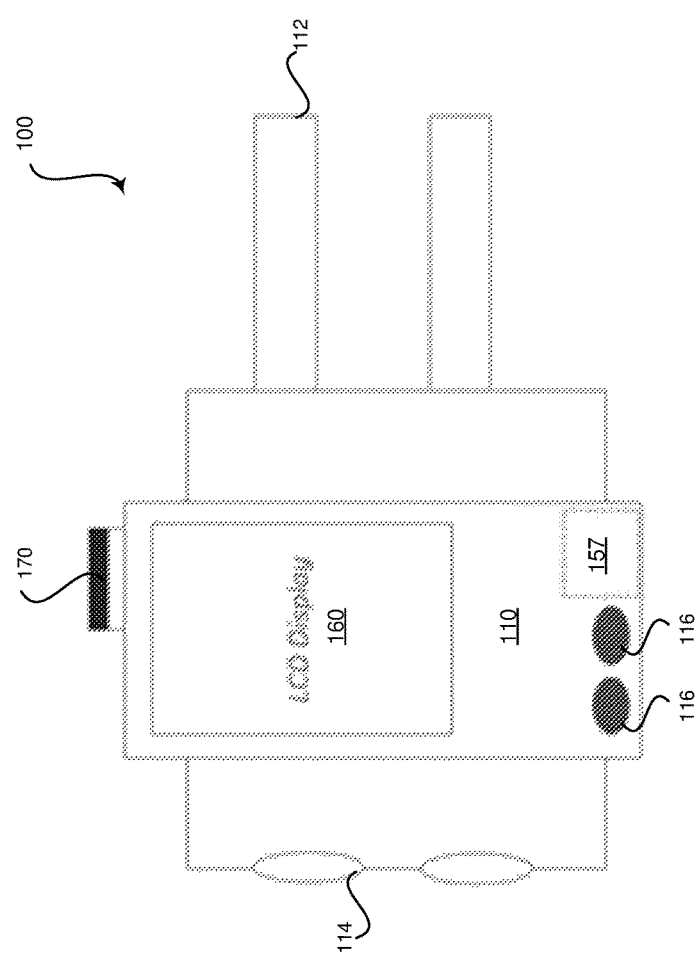
FIG. 1 illustrates an exemplary AC power supply quality monitoring system, in accordance with various embodiments.

Certain embodiments of the disclosure may be found in a method and system for monitoring quality and controlling an AC power supply provided to an ultrasound system from a power outlet. More specifically, aspects of the present disclosure have the technical effect of analyzing and presenting AC power supply quality characteristics at a display of an AC power supply quality monitoring system. Various embodiments have the technical effect of controlling the AC power supplied to an ultrasound system based on AC power supply quality characteristics determined at an AC power supply quality monitoring system. Exemplary embodiments have the technical effect of protecting an ultrasound system and preventing the acquisition of ultrasound data having image artifacts caused by AC power having AC power quality characteristics outside of a threshold quality range.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present disclosure. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an exemplary embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Furthermore, the term processor or processing unit, as used herein, refers to any type of processing unit that can carry out the calculations performed in various embodiments, such as single or multi-core: CPU, Graphics Board, DSP, FPGA, ASIC or a combination thereof.

It should be noted that various embodiments are described herein with reference to AC power provided to an ultrasound system via an AC power supply quality monitoring system. Although various examples may be provided directed to providing power to an ultrasound system, aspects of the present disclosure are not limited to this arrangement. For example, it is contemplated that the AC power supply quality monitoring system may monitor and control the AC power provided to any medical imaging device or other medical equipment. As an example, an AC power supply quality monitoring system may monitor and control the AC power provided to an X-ray imaging system, a magnetic resonance (MR) imaging system, a computed tomography (CT) imaging system, and/or any suitable medical imaging system or other medical equipment.

Figure 2:
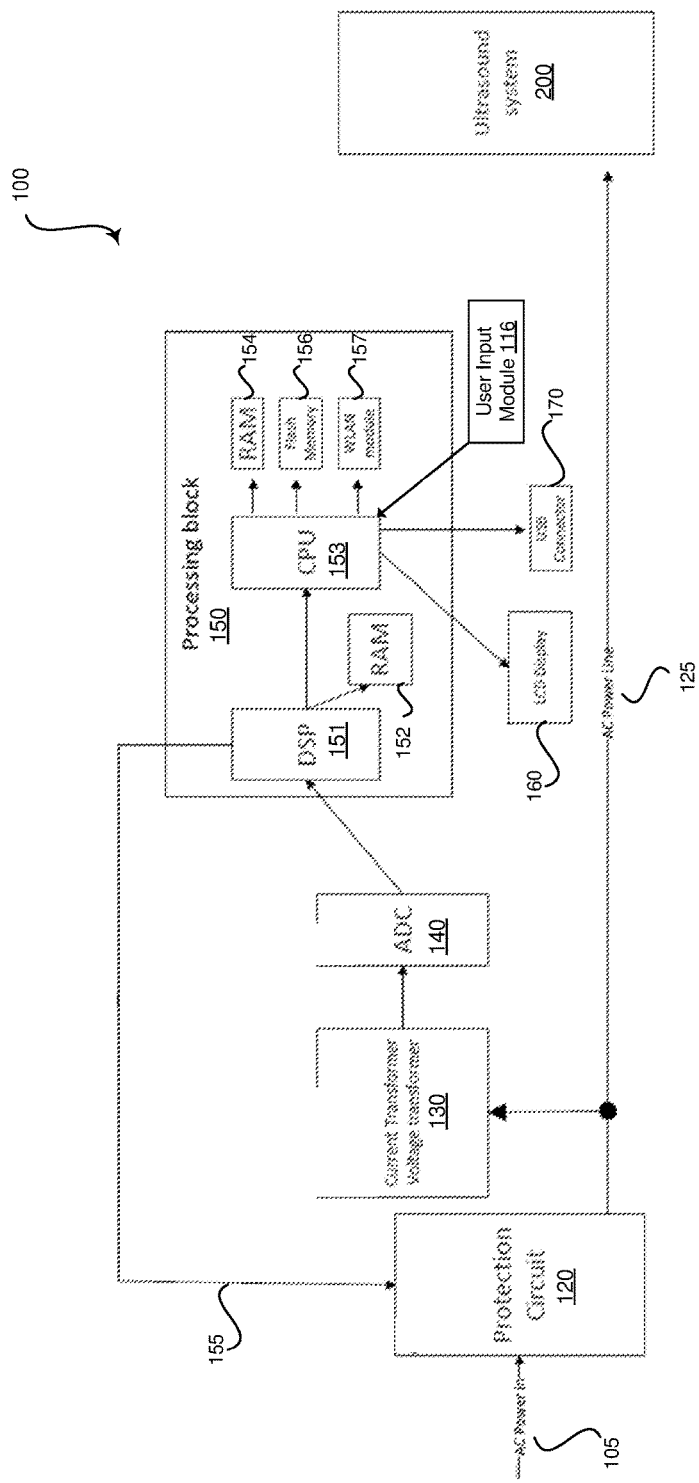
FIG. 2 is a block diagram of an exemplary AC power supply quality monitoring system, in accordance with various embodiments.

FIG. 1 illustrates an exemplary AC power supply quality monitoring system 100, in accordance with various embodiments. FIG. 2 is a block diagram of an exemplary AC power supply quality monitoring system 100, in accordance with various embodiments. Referring to FIGS. 1 and 2, the AC power supply quality monitoring system 100 comprises a plug 112, a socket 114, and a housing 110. The housing 110 may include user input modules 116, a display 160, and a Universal Serial Bus (USB) digital interface 170. The AC power supply quality monitoring system 100 may include a protection circuit 120, transformer 130, analog-to-digital (ADC) converter 140, and processing components 150 disposed in the housing 110. The processing components 150 may comprise processor(s) 151, 153, storage 152, 154, 156, and communication component(s) 157. The protection circuit 120, display 160, USB digital interface 170, and user input modules 116 may be communicatively coupled to the processor(s) 151, 153. In various embodiments, the plug 112 is configured to be inserted into a socket of a power outlet, such as a wall outlet or any suitable power supply. The plug 112 receives AC power input 105 into the AC power supply quality monitoring system 100 and provides the AC power input 105 to the protection circuit 120.

The protection circuit 120 comprises suitable logic, circuitry, interfaces and/or code that may be operable to selectively block the AC power input 105 or output the AC power input 105. For example, the protection circuit 120 may be operable to block or output the AC power input 105 in response to a control signal 155 received from the processing components 150. The protection circuit 120 may prevent the AC power input 105 from being passed on in response to a control signal activating a protection circuit block. The protection circuit 120 may output the AC power input 105 on an AC power line 125 to an ultrasound system 200 via a socket 114 and to a transformer 130 if no protection circuit block activation has been received and/or in response to a protection circuit block deactivation signal, among other things. The AC power input 105 signal output on the AC power line 125 may be provided in parallel and/or simultaneously to both the quality monitoring components 130, 140, 150 and to the ultrasound system 200 or other equipment coupled to the socket 114 of the AC power supply quality monitoring system 100.

The transformer 130 comprises suitable logic, circuitry, interfaces and/or code that may be operable to reduce the current and voltage of the AC power input 105 to values suitable for input to the ADC 140. For example, the AC power input 105 received via the protection circuit 120 on AC power line 125 may have high current and/or voltage values that may damage the ADC 140. The transformer 130 transforms the current and/or voltage of the AC power input 105 and provides the transformed AC power input to the ADC 140.

The ADC 140 may comprise suitable logic, circuitry, interfaces and/or code that may be operable to convert the transformed AC power input from the transformer 130 to a corresponding digital signal. The ADC 140 is disposed between the transformer 130 and the processing components 150. Notwithstanding, the disclosure is not limited in this regard. Accordingly, in some embodiments, the ADC may be integrated within the transformer 130 and/or processing components 150.

The processing components 150 may include processor(s) 151, 153, storage 152, 154, 156. The processing components 150 may include and/or be communicatively coupled to communications components 157, 170, a user input module 116, and a display system 160. The processing components 150 may include and/or be communicatively coupled to any number of processors 151, 153, storage components 152, 154, 156, user input modules 116, communication components 157, 170, and display systems 160 and is not in any way limited to the embodiment of system 100 illustrated in FIGS. 1 and 2. The processing components 150 may communicate via wired and/or wireless communication, for example, and may be separate systems and/or integrated to varying degrees, for example.

The storage 152, 154, 156 comprises suitable logic, circuitry, interfaces and/or code that may be operable to store a quality monitoring application, AC power quality characteristic thresholds, storage settings, display system presentation settings, communication component data transfer settings, and/or any suitable information. The storage 152, 154, 156 may be one or more computer-readable memories, for example, such as a random access memory, flash memory, hard disk, floppy disk, CD, CD-ROM, DVD, compact storage, read-only memory, electrically erasable and programmable read-only memory and/or any suitable memory. The storage 152, 154, 156 may include databases, libraries, sets of information, or other storage accessed by and/or incorporated with the processor 151, 153, for example. The storage 152, 154, 156 may be able to store data temporarily or permanently, for example. In various embodiments, the storage 152, 154, 156 stores one or more sets of software instructions, such as instructions for analyzing AC power quality characteristics, controlling the protection circuit in response to the analyzed characteristics, and presenting the analyzed characteristics at the display system 160. In a representative embodiment, the storage 152, 154, 156 may store AC power quality characteristics thresholds for application during analysis of the digital signal representative of the AC power input 105. In certain embodiments, storage 152, 154, 156 may include cloud storage accessible over a network.

The processor(s) 151, 153 comprises suitable logic, circuitry, interfaces and/or code that may be operable to analyze a digital signal corresponding with the AC power input 105 to determine AC power supply quality characteristics. The processor(s) 151, 153 may be operable to compare the AC power supply quality characteristics to thresholds stored in storage 152, 154, 156 to determine whether the AC power input 105 is of sufficient quality to pass on to the ultrasound system 200 or other medical equipment. The processor(s) 151, 153 may be configured to send a block activation signal 155 to protection circuit 120 if the AC power supply quality characteristics are outside of the thresholds (e.g., exceed upper thresholds and/or fall below lower thresholds). The processor(s) 151, 153 may be configured to send alerts to the ultrasound system 200 or any suitable computing device communicatively coupled with the AC power supply quality monitoring system 100 via the communications component(s) 157, 170 if the AC power supply quality characteristics are outside of the thresholds. In various embodiments, the ultrasound system 200 or other medical equipment may be automatically and/or manually switched to an alternate power source, such as a battery, Uninterruptible Power Supply (UPS), or the like, in response to a notification that the AC power supply quality characteristics are outside of the thresholds. The processor(s) 151, 153 may be configured to present the AC power supply quality characteristics and/or alerts at the display system 160. The processor(s) 151, 153 may be configured to send the AC power supply quality characteristics to the ultrasound system 200 or any suitable computing device communicatively coupled with the AC power supply quality monitoring system 100 via the communications component(s) 157, 170. The processor 151, 153 may be one or more digital signal processors, central processing units, microprocessors, microcontrollers, and/or the like. The processor 151, 153 may be an integrated component, or may be distributed across various locations, for example. The processor 151, 153 may be capable of executing any of the method(s) 300 and/or set(s) of instructions discussed below in accordance with the present disclosure, for example.

The communications component(s) 157, 170 may be a wired connection 170 (e.g., Universal Serial Bus (USB) digital interface, etc.), a wireless connection 157 (e.g., Bluetooth, Wi-Fi, etc.), or any suitable connection. The communication component(s) 157, 170 comprises suitable logic, circuitry, interfaces and/or code that may be operable to communicate information from storage 152, 154, 156 at the direction of the processor(s) 151, 153 of the AC power supply quality monitoring system 100. For example, the communications component(s) 157, 170 may transmit stored AC power quality characteristics and/or alerts corresponding to when AC power quality characteristics move outside of pre-defined thresholds, among other things. In an exemplary embodiment, the AC power quality characteristics and/or alerts may be transmitted to a connected computer of a service technician, to the ultrasound system 200, and/or the like. In various embodiments, the AC power supply quality monitoring system 100 may be powered by the AC power input 105, an internal battery, an external battery/power supply, a computer via the communications component 170, and/or any suitable power source.

The user input module 116 comprises suitable logic, circuitry, interfaces and/or code that may be operable to communicate information from a user and/or at the direction of the user to the processing component 150 of the AC power supply quality monitoring system 100, for example. The user input module 116 may include button(s), a touchscreen, and/or any other device capable of receiving a user directive. In certain embodiments, one or more of the user input modules 116 may be integrated into other components, such as the display system 160, for example. As an example, user input module 116 may include a touchscreen display. In certain embodiments, the user input module 116 may provide instructions for analyzing AC power quality characteristics of a digital signal corresponding with an AC power input 105. In various embodiments, the user input module 116 may provide instructions for displaying, storing, and/or communicating the determined AC power quality characteristics of the digital signal corresponding with the AC power input 105. In an exemplary embodiment, the user input module 116 may provide AC power quality characteristics threshold parameters, such as acceptable voltage variations (e.g., +/−5%), frequency variations (e.g., +/−1%), voltage unbalance (e.g., within 3%), harmonic distortion, amount of acceptable electrical noise (e.g., lower than 200 kHz), a power factor, amount of power consumption, and the like. The AC power quality characteristics threshold parameters provided at the user input module 116 may be stored in storage 152, 154, 156. The AC power quality characteristics threshold parameters stored in storage 152, 154, 156 may be applied by the processor 151, 153 to determine whether to send a block activation signal 155 to the protection circuit 120 for preventing the AC power input 105 from being provided to the ultrasound system 200, for example.

The display system 160 comprises suitable logic, circuitry, interfaces and/or code that may be operable to communicate visual information to a user. For example, a display system 160 may include one or more displays comprising a liquid crystal display, a light emitting diode display, and/or any suitable display. The display system 160 can be integrated with the user input module 116 to form a touchscreen display. The display system 160 may be operable to display alerts and/or AC power supply quality characteristics selected and/or processed by processor(s) 151, 153, for example. The AC power supply quality characteristics presented at the display system 160 may include current characteristics and/or logged historical characteristics. In various embodiments, the user input module 116 may be manipulated to navigate the presentation of the alerts and/or AC power supply quality characteristics presented at the display system 160.

Figure 3:
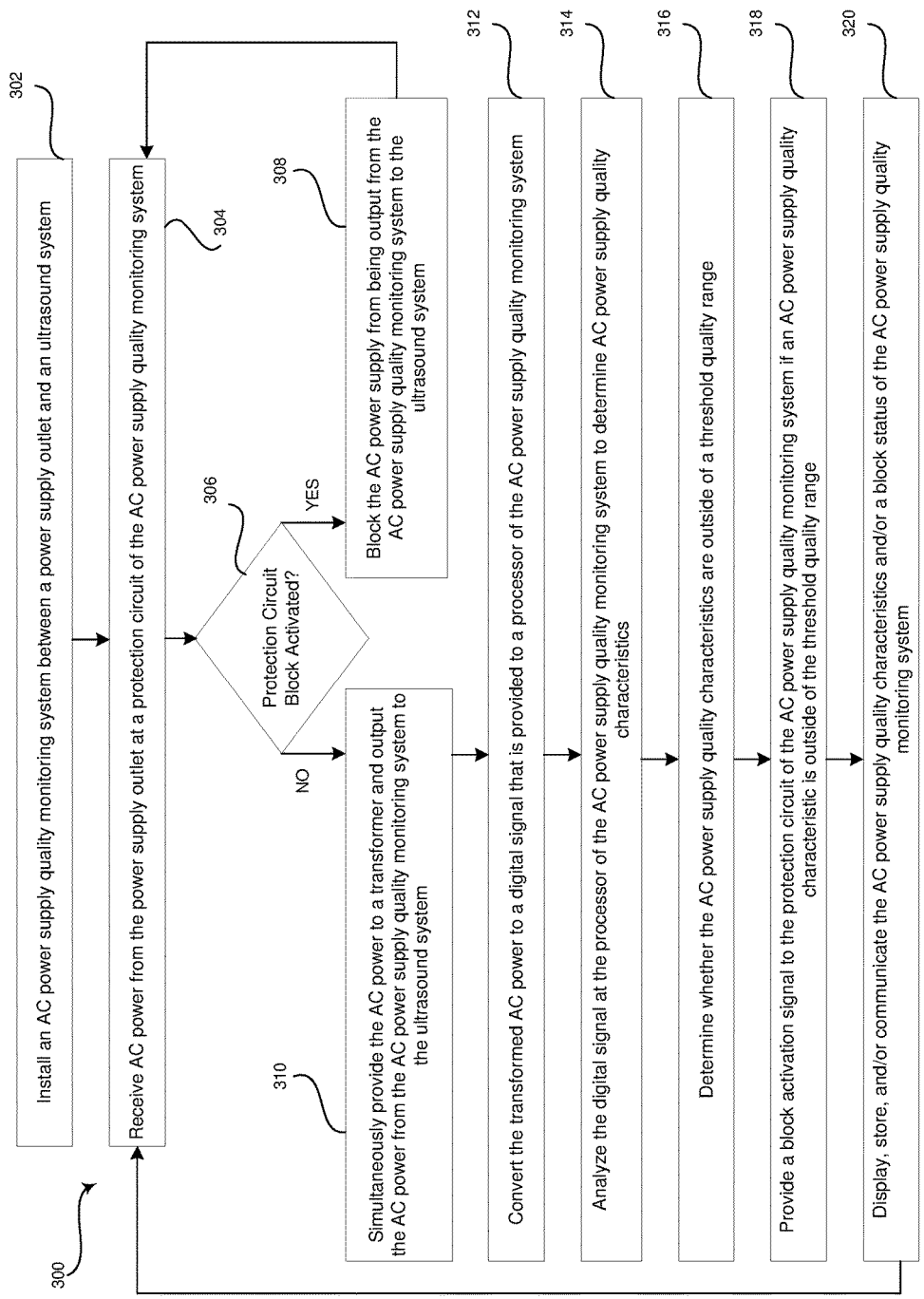
FIG. 3 is a flow chart illustrating exemplary steps that may be utilized for monitoring quality and controlling an AC power supply provided to an ultrasound system from a power outlet, in accordance with various embodiments.

FIG. 3 is a flow chart 300 illustrating exemplary steps 302-320 that may be utilized for monitoring quality and controlling an AC power supply provided to an ultrasound system 200 from a power outlet, in accordance with various embodiments. Referring to FIG. 3, there is shown a flow chart 300 comprising exemplary steps 302 through 320. Certain embodiments of the present disclosure may omit one or more of the steps, and/or perform the steps in a different order than the order listed, and/or combine certain of the steps discussed below. For example, some steps may not be performed in certain embodiments of the present disclosure. As a further example, certain steps may be performed in a different temporal order, including simultaneously, than listed below.

At step 302, an AC power supply quality monitoring system 100 is installed between a power supply outlet and an ultrasound system 200 or any suitable medical equipment. For example, the AC power supply quality monitoring system 100 may comprise a plug 112 that may be inserted directly or indirectly into a socket of the power outlet or other power supply. The ultrasound system 200 or other suitable medical equipment may be coupled to the AC power supply quality monitoring system 100 by inserting a plug of the ultrasound system 200 or other suitable medical equipment into a socket 114 of the AC power supply quality monitoring system 100.

At step 304, a protection circuit 120 of the AC power supply quality monitoring system 100 receives an AC power input 105 from the power supply outlet. For example, the AC power input 105 from a power outlet may be provided to the protection circuit 120 via a plug 112 of the AC power supply quality monitoring system 100.

At step 306, if a block is activated at the protection circuit 120 of the AC power supply quality monitoring system 100, the method proceeds to step 308. If the block is not activated at the protection circuit 120 of the AC power supply quality monitoring system 100, the method proceeds to step 310. In various embodiments, the block may be activated in response to a control signal 155 from processing components 150 of the AC power supply quality monitoring system 100.

At step 308, if it is determined that the block is activated at step 306, the protection circuit 120 prevents the AC power input 105 from being output from the AC power supply quality monitoring system 100 to the ultrasound system 200 or other medical equipment. The AC power input 105 may be blocked, for example, to prevent damage to the ultrasound system 200 or other medical equipment and/or to prevent image artifacts caused by a poor quality AC power input 105. The block may be provided by a switch or any suitable mechanism for disconnecting the AC power supply from the ultrasound system 200 or other medical equipment.

At step 310, if it is determined that the block is not activated at step 306, the protection circuit 120 simultaneously provides the AC power input 105 to a transformer 130 of the AC power supply quality monitoring system 100 and outputs the AC power input 105 from the AC power supply quality monitoring system 100 to the ultrasound system 200 or other medical equipment. For example, the protection circuit 120 may provide the AC power input 105 on an AC power line 125 that carries the AC power input 105 to the socket 114 and to the transformer 130. The protection circuit 120 may continuously output the AC power input 105 unless and/or until the protection circuit 120 receives a block activation control signal 155 from the processing components 150.

At step 312, the AC power input 105 is transformed and converted to a digital signal that is provided to processing component(s) 150 of the AC power supply quality monitoring system 100. For example, the transformer 130 may reduce the voltage and/or current of the AC power input 105 to a level suitable for input to an analog-to-digital converter (ADC) 140. The ADC 140 may convert the transformed AC power input 105 into a digital signal that is provided to a digital signal processor (DSP) 151 of the processing component(s) 150.

At step 314, the digital signal received at the digital signal processor 151 of the processing component(s) 150 is analyzed by the digital signal processor 151 to determine AC power supply quality characteristics. For example, the digital signal processor 151 may evaluate one or more of the voltage, frequency, voltage unbalance, voltage and/or current harmonic distortion, electrical noise, power factor, power consumption, and the like. The quality characteristics representative of the quality of the AC power input 105 may be extracted and analyzed from the digital signal. The quality characteristics for analysis may be selected by default programs and/or as specified by instructions received from the user input module 116 and/or via wireless 157 or wired communications 170.

At step 316, the processing component(s) 150 determine whether the AC power supply quality characteristics are outside of a threshold quality range. For example, upper limits and/or lower limits for one or more of the quality characteristics may be stored in RAM 152, 154, flash memory 156, or any suitable storage. The digital signal processor 151 and/or central processing unit 153 may compare the threshold limits to the AC power supply quality characteristics analyzed at step 314. As an example, the amplitude of the voltage analyzed at step 314 may be compared to +/−5% thresholds of the country-dependent standard operating voltage (e.g., 120 Volts in the United States). The frequency may be compared to +/−1% thresholds of the country-dependent frequency (e.g., 60 Hz in the United States). The voltage unbalance may be compared to a threshold of within 3%. The electrical noise may be compared to a threshold of less than 200 kHz. In various embodiments, one or more of harmonic distortion (voltage), harmonic distortion (current), power factor, and power consumption may additionally and/or alternatively include threshold values for comparison. The thresholds may be default thresholds, such as being based on International Electrotechnical Commission (IEC), American National Standards Institute (ANSI), or any suitable standard. In certain embodiments, thresholds may be adjusted based on the environment and/or medical equipment. For example, the quality thresholds for comparison may be specified and/or adjusted by instructions received from the user input module 116 and/or via wireless 157 or wired communications 170.

At step 318, a block activation signal is provided to the protection circuit 120 of the AC power supply quality monitoring system 100 if an AC power supply quality characteristic is outside of the threshold quality range. For example, if at step 316 the processor(s) 151, 153 determine that one or more AC power supply quality characteristics are above a threshold upper limit and/or below a threshold lower limit, the digital signal processor 151 may send a block activation control signal to the protection circuit 120 to prevent the AC power input 105 from continuing to be provided to the ultrasound system 200 or other medical equipment. The AC power supply quality monitoring system 100 may prevent damage from occurring to the ultrasound machine 200 or other medical equipment and/or may prevent the ultrasound system 200 from generating images having artifacts caused by poor AC power supply quality.

At step 320, the AC power supply quality characteristics and/or block status of the AC power supply quality monitoring system 100 may be displayed, stored, and/or communicated. For example, the quality characteristics determined from the digital signal may be stored by the digital signal processor 151 at RAM 152 and/or may be provided to central processing unit (CPU) 153 for storage at RAM 154 and/or flash memory 156. The quality characteristics may additionally and/or alternatively be communicated via the WLAN module 157 and/or USB connector 170, and/or presented at display system 160. As an example, a user may monitor the AC power input 105 characteristics by navigating through the characteristics and/or alerts presented at the display system 160 with the user input module 116. In various embodiments, an ultrasound operator may review AC power input 105 characteristics and/or alerts transmitted to and displayed at the ultrasound system 200 via communications component(s) 157, 170. In certain embodiments, AC power input 105 characteristics and/or alerts may be transmitted and presented to a computing device of a service technician or service center via communications component(s) 157, 170.

In an exemplary embodiment, steps 304 through 320 may be repeated continuously until the AC power supply quality monitoring system 100 is uninstalled and/or disconnected.

Aspects of the present disclosure provide a system 100 and method 300 for monitoring quality and controlling an AC power supply provided to an ultrasound system 200 or other medical equipment from a power outlet. In accordance with various embodiments, a method 300 may comprise receiving 304 an alternating current (AC) power input 105 at a protection circuit 120 of an AC power supply quality monitoring system 100. The method 300 may comprise providing 310 the AC power input 105 to conversion circuitry 130, 140 and to an output 114 of the AC power supply quality monitoring system 100 if 306 the protection circuit 120 is in a normal operating mode. The method 300 may comprise converting 312, by the conversion circuitry 130, 140, the AC power input 105 to a digital signal representative of the AC power input 105. The method 300 may comprise analyzing 314, by a processor 151, 153, the digital signal to determine AC power supply quality characteristics of the AC power input 105. The method 300 may comprise presenting 320, at a display system 160 of the AC power supply quality monitoring system 100, the AC power supply quality characteristics of the AC power input 105. The method 300 may comprise determining 316, by the processor 151, 153, whether the AC power supply quality characteristics are within a threshold quality range. The method 300 may comprise activating 318 a block at the protection circuit 120 to change the operating mode from the normal operating mode to a blocked operating mode if the AC power supply quality characteristics are outside of the threshold quality range. The protection circuit prevents 308 the AC power input 105 from being provided to the output 114 of the AC power supply quality monitoring system 100 if 306 the protection circuit is in the blocked operating mode.

In an exemplary embodiment, the method 300 may comprise installing 302 the AC power supply quality monitoring system 100 between a power supply outlet and medical equipment 200. In a representative embodiment, the AC power supply quality monitoring system 100 may be installed by inserting a plug 112 of the AC power supply quality monitoring system 100 into a socket of the power outlet and inserting a plug of the medical equipment 200 into a socket 114 of the AC power supply quality monitoring system 100. The socket 114 is the output of the AC power supply quality monitoring system 100. In various embodiments, the medical equipment is an ultrasound system 200.

In certain embodiments, the method 300 may comprise storing 320 the AC power supply quality characteristics at storage 152, 154, 156 of the AC power supply quality monitoring system 100. In an exemplary embodiment, the method 300 may comprise wirelessly transmitting 320, 157 the AC power supply quality characteristics to an external system. In a representative embodiment, the method 300 may comprise transmitting 320 the AC power supply quality characteristics to an external system via a Universal Serial Bus (USB) connector 170. In various embodiments, the method 300 may comprise receiving an instruction at the processor 151, 153 from a user input module 116 to one or more of navigate the AC power supply quality characteristics presented at the display system 160, select one or more of the AC power supply quality characteristics for analysis by the processor 151, 153, and define the threshold quality range for one or more of the AC power supply quality characteristics. In certain embodiments, the AC power supply quality characteristics comprises a plurality of: a voltage, a frequency, a voltage unbalance, voltage harmonic distortion, current harmonic distortion, electrical noise, power factor, and power consumption.

In accordance with various embodiments, an alternating current (AC) power supply quality monitoring system 100 may comprise a protection circuit 120, conversion circuitry 130, 140, a processor 151, 153, and a display system 160. The protection circuit 120 may be operable to receive an AC power input 105. The protection circuit 120 may be operable to provide the AC power input 105 to the conversion circuitry 130, 140 and to an output 114 of the AC power supply quality monitoring system 100 if the protection circuit 120 is in a normal operating mode. The protection circuit 120 may be operable to prevent the AC power input 105 from being provided to the output 114 of the AC power supply quality monitoring system 100 if the protection circuit 120 is in a blocked operating mode. The conversion circuitry 130, 140 may be operable to convert the AC power input 105 to a digital signal representative of the AC power input 105. The processor 151, 153 may be configured to analyze the digital signal to determine AC power supply quality characteristics of the AC power input 105. The processor 151, 153 may be configured to determine whether the AC power supply quality characteristics are within a threshold quality range. The processor 151, 153 may be configured to activate a block at the protection circuit 120 to change the operating mode from the normal operating mode to the blocked operating mode if the AC power supply quality characteristics are outside of the threshold quality range. The display system 160 may be operable to present the AC power supply quality characteristics of the AC power input 105.

In a representative embodiment, the AC power supply quality monitoring system 100 may comprise a plug 112 operable for insertion into a socket of a power outlet to receive the AC power input 105. In various embodiments, the AC power supply quality monitoring system 100 may comprise a socket 114 operable to receive the insertion of a plug of medical equipment 200. The socket 114 may be the output of the AC power supply quality monitoring system 100. In certain embodiments, the AC power supply quality monitoring system 100 may comprise one or more communication components 157, 170 operable to transmit the AC power supply quality characteristics to an external system. The one or more communication components 157, 170 may comprise one or both of a wireless communication component 157 and a wired communication component 170. In an exemplary embodiment, the AC power supply quality monitoring system 100 may comprise a housing 110. The protection circuit 120, the conversion circuitry 130, 140, and the processor 151, 153 may be disposed in the housing 110. The display system 160 may be disposed on the housing 110. In a representative embodiment, the AC power supply quality monitoring system 100 may comprise a user input module 116 operable to provide instructions to one or more of navigate the AC power supply quality characteristics presented at the display system 160, select one or more of the AC power supply quality characteristics for analysis by the processor 151, 153, and define the threshold quality range for one or more of the AC power supply quality characteristics.

Certain embodiments provide a non-transitory computer readable medium having stored computer program comprises at least one code section that is executable by a machine for causing the machine to perform steps 300 disclosed herein. Exemplary steps 300 may comprise analyzing 314 a digital signal to determine AC power supply quality characteristics of a corresponding AC power input 105 received and converted to the digital signal at an AC power supply quality monitoring system 100. The steps 300 may comprise presenting 320 the AC power supply quality characteristics of the AC power input 105 at a display system 160 of the AC power supply quality monitoring system 100. The steps 300 may comprise determining 316 whether the AC power supply quality characteristics are within a threshold quality range. The steps 300 may comprise activating 318 a block at a protection circuit 120 of the AC power supply quality monitoring system 100 if the AC power supply quality characteristics are outside of the threshold quality range. The block at the protection circuit 120 prevents the AC power input 105 from being output from the AC power supply quality monitoring system 100.

In various embodiments, the steps 300 may comprise storing 320 the AC power supply quality characteristics at storage 152, 154, 156 of the AC power supply quality monitoring system 100. In certain embodiments, the steps 300 may comprise wirelessly transmitting 320 the AC power supply quality characteristics to an external system. In an exemplary embodiment, the steps 300 may comprise transmitting 320 the AC power supply quality characteristics to an external system via a Universal Serial Bus (USB) connector 170. In a representative embodiment, the steps 300 may comprise, in response to a received instruction, one or more of: navigating the AC power supply quality characteristics presented at the display system 160, selecting one or more of the AC power supply quality characteristics for analysis, and defining the threshold quality range for one or more of the AC power supply quality characteristics.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "configured" and/or "operable" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for monitoring quality and controlling an AC power supply provided to an ultrasound system from a power outlet.

Accordingly, certain embodiments may be realized in hardware, software, or a combination of hardware and software. Various embodiments may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method, comprising:
    receiving an alternating current (AC) power input at a protection circuit of an AC power supply quality monitoring system;
    providing the AC power input to conversion circuitry and to an output of the AC power supply quality monitoring system if the protection circuit is in a normal operating mode;
    converting, by the conversion circuitry, the AC power input to a digital signal representative of the AC power input;
    analyzing, by a processor, the digital signal to determine AC power supply quality characteristics of the AC power input;
    presenting, at a display system of the AC power supply quality monitoring system, the AC power supply quality characteristics of the AC power input;
    determining, by the processor, whether the AC power supply quality characteristics are within a threshold quality range; and
    activating a block at the protection circuit to change the operating mode from the normal operating mode to a blocked operating mode if the AC power supply quality characteristics are outside of the threshold quality range, wherein the protection circuit prevents the AC power input from being provided to the output of the AC power supply quality monitoring system if the protection circuit is in the blocked operating mode.

2. The method of claim 1, comprising installing the AC power supply quality monitoring system between a power supply outlet and medical equipment.

3. The method of claim 2, wherein the AC power supply quality monitoring system is installed by:
    inserting a plug of the AC power supply quality monitoring system into a socket of the power outlet, and
    inserting a plug of the medical equipment into a socket of the AC power supply quality monitoring system, wherein the socket is the output of the AC power supply quality monitoring system.

4. The method of claim 3, wherein the medical equipment is an ultrasound system.

5. The method of claim 1, comprising storing the AC power supply quality characteristics at storage of the AC power supply quality monitoring system.

6. The method of claim 1, comprising wirelessly transmitting the AC power supply quality characteristics to an external system.

7. The method of claim 1, comprising transmitting the AC power supply quality characteristics to an external system via a Universal Serial Bus (USB) connector.

8. The method of claim 1, comprising receiving an instruction at the processor from a user input module to one or more of:
- navigate the AC power supply quality characteristics presented at the display system,
- select one or more of the AC power supply quality characteristics for analysis by the processor, and
- define the threshold quality range for one or more of the AC power supply quality characteristics.

9. The method of claim 1, wherein the AC power supply quality characteristics comprises a plurality of:
- a voltage,
- a frequency,
- a voltage unbalance,
- voltage harmonic distortion,
- current harmonic distortion,
- electrical noise,
- power factor, and
- power consumption.

10. An alternating current (AC) power supply quality monitoring system, comprising:
- a protection circuit operable to:
  - receive an AC power input,
  - provide the AC power input to conversion circuitry and to an output of the AC power supply quality monitoring system if the protection circuit is in a normal operating mode, and
  - prevent the AC power input from being provided to the output of the AC power supply quality monitoring system if the protection circuit is in a blocked operating mode;
- the conversion circuitry operable to convert the AC power input to a digital signal representative of the AC power input;
- a processor configured to:
  - analyze the digital signal to determine AC power supply quality characteristics of the AC power input,
  - determine whether the AC power supply quality characteristics are within a threshold quality range, and
  - activate a block at the protection circuit to change the operating mode from the normal operating mode to the blocked operating mode if the AC power supply quality characteristics are outside of the threshold quality range; and
- a display system operable to present the AC power supply quality characteristics of the AC power input.

11. The AC power supply quality monitoring system of claim 10, comprising a plug operable for insertion into a socket of a power outlet to receive the AC power input.

12. The AC power supply quality monitoring system of claim 10, comprising a socket operable to receive the insertion of a plug of medical equipment, wherein the socket is the output of the AC power supply quality monitoring system.

13. The AC power supply quality monitoring system of claim 10, comprising one or more communication components operable to transmit the AC power supply quality characteristics to an external system, wherein the one or more communication components comprises one or both of a wireless communication component and a wired communication component.

14. The AC power supply quality monitoring system of claim 10, comprising a housing, wherein:
- the protection circuit, the conversion circuitry, and the processor are disposed in the housing, and
- the display system is disposed on the housing.

15. The AC power supply quality monitoring system of claim 10, comprising a user input module operable to provide instructions to one or more of:
- navigate the AC power supply quality characteristics presented at the display system,
- select one or more of the AC power supply quality characteristics for analysis by the processor, and
- define the threshold quality range for one or more of the AC power supply quality characteristics.

16. A non-transitory computer readable medium having stored thereon, a computer program having at least one code section, the at least one code section being executable by a machine for causing the machine to perform steps comprising:
- analyzing a digital signal to determine AC power supply quality characteristics of a corresponding AC power input received and converted to the digital signal at an AC power supply quality monitoring system;
- presenting the AC power supply quality characteristics of the AC power input at a display system of the AC power supply quality monitoring system;
- determining whether the AC power supply quality characteristics are within a threshold quality range; and
- activating a block at a protection circuit of the AC power supply quality monitoring system if the AC power supply quality characteristics are outside of the threshold quality range, wherein the block at the protection circuit prevents the AC power input from being output from the AC power supply quality monitoring system.

17. The non-transitory computer readable medium of claim 16, comprising storing the AC power supply quality characteristics at storage of the AC power supply quality monitoring system.

18. The non-transitory computer readable medium of claim 16, comprising wirelessly transmitting the AC power supply quality characteristics to an external system.

19. The non-transitory computer readable medium of claim 16, comprising transmitting the AC power supply quality characteristics to an external system via a Universal Serial Bus (USB) connector.

20. The non-transitory computer readable medium of claim 16, comprising, in response to a received instruction, one or more of:
- navigating the AC power supply quality characteristics presented at the display system,
- selecting one or more of the AC power supply quality characteristics for analysis, and
- defining the threshold quality range for one or more of the AC power supply quality characteristics.

* * * * *